United States Patent
Katayama et al.

(10) Patent No.: US 12,178,413 B2
(45) Date of Patent: Dec. 31, 2024

(54) TRACE AMOUNT LIQUID SAMPLE COLLECTOR

(71) Applicant: Provigate Inc., Tokyo (JP)

(72) Inventors: Norikazu Katayama, Tokyo (JP); Narushi Ito, Tokyo (JP)

(73) Assignee: Provigate Inc., Tokyo (JP)

( * ) Notice: Subject to any disclaimer, the term of this patent is extended or adjusted under 35 U.S.C. 154(b) by 1043 days.

(21) Appl. No.: 17/041,809

(22) PCT Filed: Mar. 25, 2019

(86) PCT No.: PCT/JP2019/012357
§ 371 (c)(1),
(2) Date: Sep. 25, 2020

(87) PCT Pub. No.: WO2019/188900
PCT Pub. Date: Oct. 3, 2019

(65) Prior Publication Data
US 2021/0007720 A1    Jan. 14, 2021

(30) Foreign Application Priority Data

Mar. 30, 2018 (JP) .................................. 2018-066585

(51) Int. Cl.
*A61B 10/00* (2006.01)

(52) U.S. Cl.
CPC ...... *A61B 10/0045* (2013.01); *A61B 10/0051* (2013.01); *A61B 2010/0067* (2013.01)

(58) Field of Classification Search
CPC ............ A61B 10/0045; A61B 10/0051; A61B 2010/0067; A61B 3/101; A61B 3/10;
(Continued)

(56) References Cited

U.S. PATENT DOCUMENTS

2006/0188410 A1    8/2006  Ishida et al.
2008/0255474 A1   10/2008  Ishida et al.
(Continued)

FOREIGN PATENT DOCUMENTS

JP    2005253700 A    9/2005
JP    2006234446 A    9/2006
(Continued)

OTHER PUBLICATIONS

Wikimedia Foundation. (Sep. 15, 2023). Rayon. Wikipedia. https://en.wikipedia.org/wiki/Rayon (Year: 2002).*
(Continued)

*Primary Examiner* — Matthew Kremer
*Assistant Examiner* — Elina Sohyun Ahn
(74) *Attorney, Agent, or Firm* — Myers Bigel, P.A.

(57) ABSTRACT

The objective of the present invention is to provide a liquid sample collector capable of collecting a trace amount of a specimen such as a tear safely and in an adequate amount. This trace amount liquid sample collector is characterized in that: the liquid sample collector is provided with a main body and a first absorbent body; the main body has at least one open end portion; the main body includes a hydrophobic material having elasticity; the first absorbent body is disposed at least partially inside the main body; the first absorbent body includes a water-absorbent material; and the first absorbent body is disposed in such a way as to be capable of coming into contact with the outside by way of the at least one open end portion of the main body.

15 Claims, 8 Drawing Sheets

(58) Field of Classification Search
CPC ........ A61B 5/4277; G01N 1/10; G01N 33/48; G01N 1/14; G01N 33/50; A61G 13/102; B32B 27/12; B01L 2400/049; B01L 3/0293

See application file for complete search history.

(56) References Cited

U.S. PATENT DOCUMENTS

| | | | |
|---|---|---|---|
| 2012/0329145 A1* | 12/2012 | Lee | G01N 33/54386 435/288.3 |
| 2016/0074019 A1 | 3/2016 | Hata et al. | |
| 2018/0052084 A1* | 2/2018 | Jones | G01N 1/405 |
| 2018/0168490 A1* | 6/2018 | Jones | A61B 5/7282 |

FOREIGN PATENT DOCUMENTS

| | | | | |
|---|---|---|---|---|
| JP | 2008259590 A | 10/2008 | | |
| JP | 2009085839 A | 4/2009 | | |
| JP | 2010243435 A | 10/2010 | | |
| JP | 2010276412 A | 12/2010 | | |
| JP | 2012026997 A | 2/2012 | | |
| JP | 2012032228 A | 2/2012 | | |
| JP | 2016507760 A | 3/2016 | | |
| JP | 2017129509 A | 7/2017 | | |
| JP | 2017216951 A | 12/2017 | | |
| WO | 2014057701 A1 | 4/2014 | | |
| WO | 2014134209 A1 | 9/2014 | | |
| WO | WO-2017177886 A1 * | 10/2017 | ............. | A61B 5/151 |
| WO | WO-2017179919 A1 * | 10/2017 | ......... | A61B 10/0096 |

OTHER PUBLICATIONS

Extended European Search Report corresponding to European Patent Application No. 19776745.2 (8 pages) (dated Nov. 12, 2021).
English translation of International Search Report corresponding to International Patent Application No. PCT/JP2019/012357 (2 pages) (mailed Jun. 25, 2019).

* cited by examiner

[Figure 1]
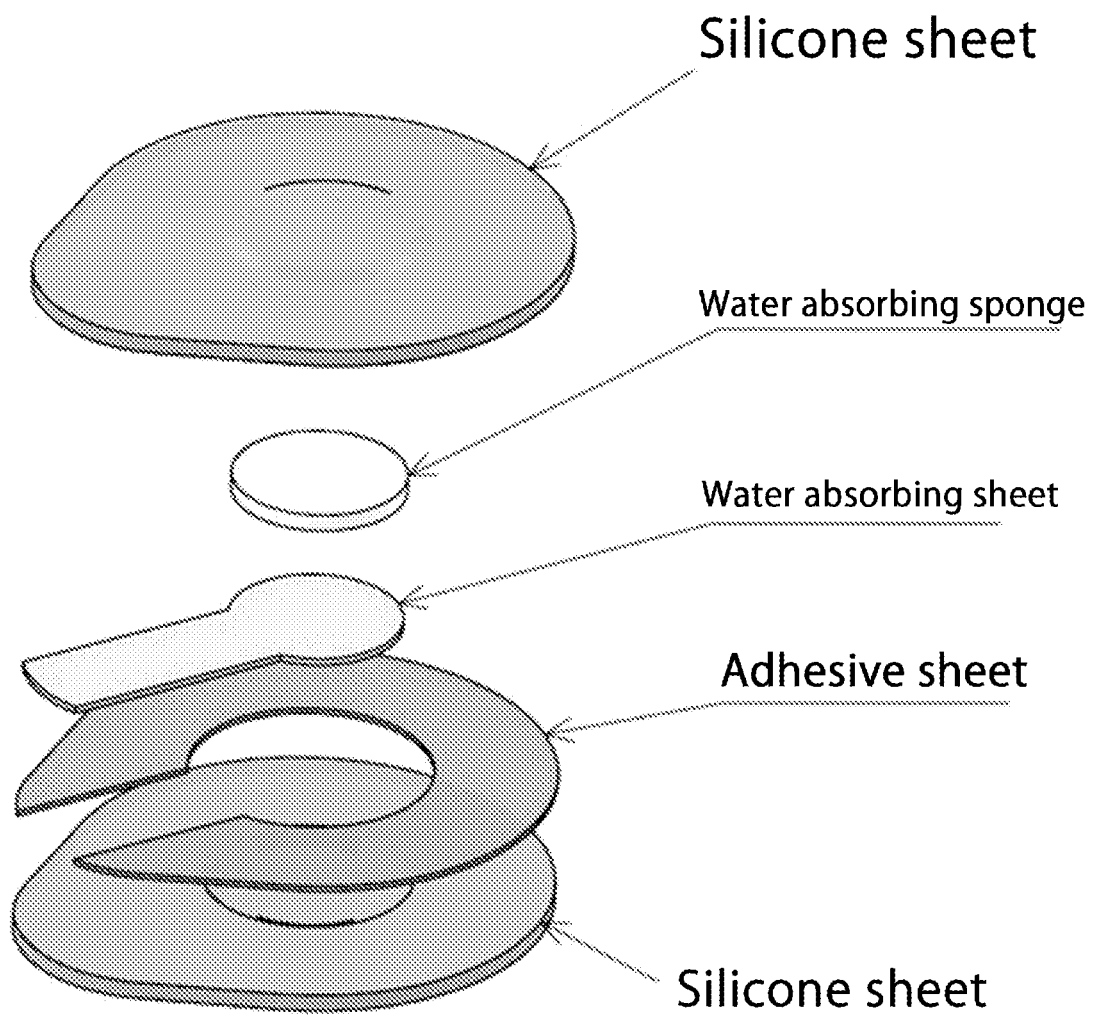

[Figure 2]
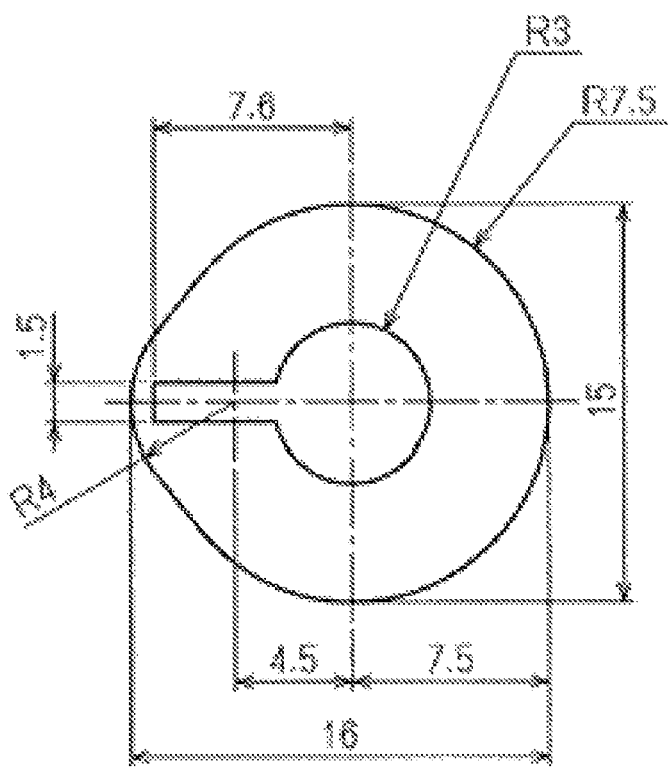

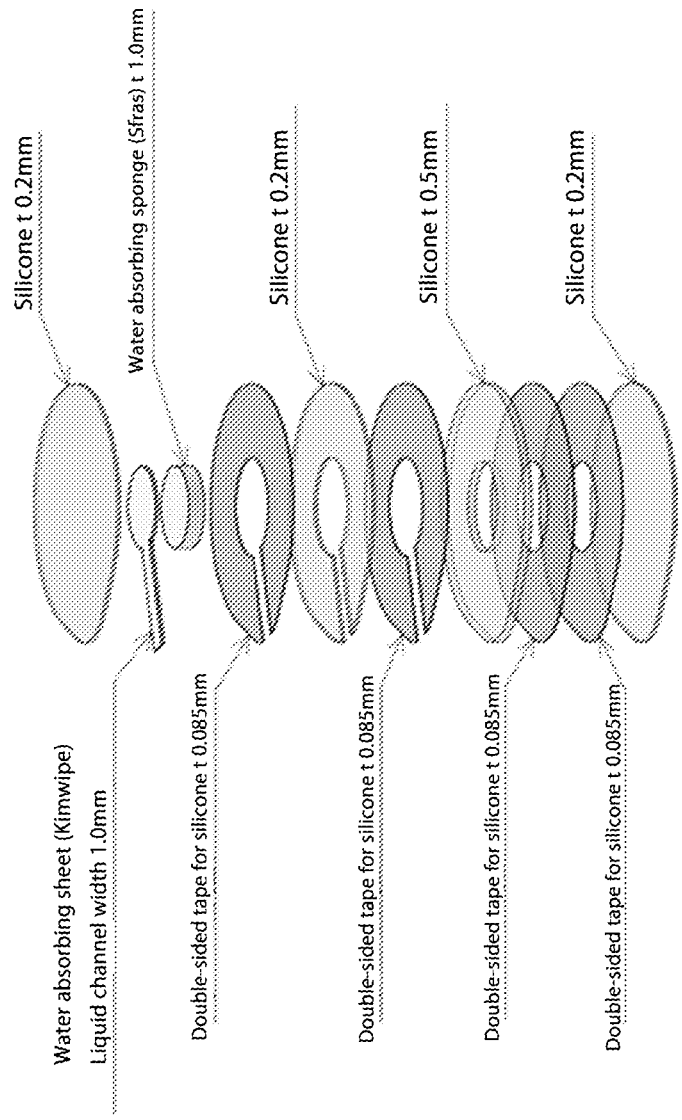
[Figure 3]

[Figure 4]
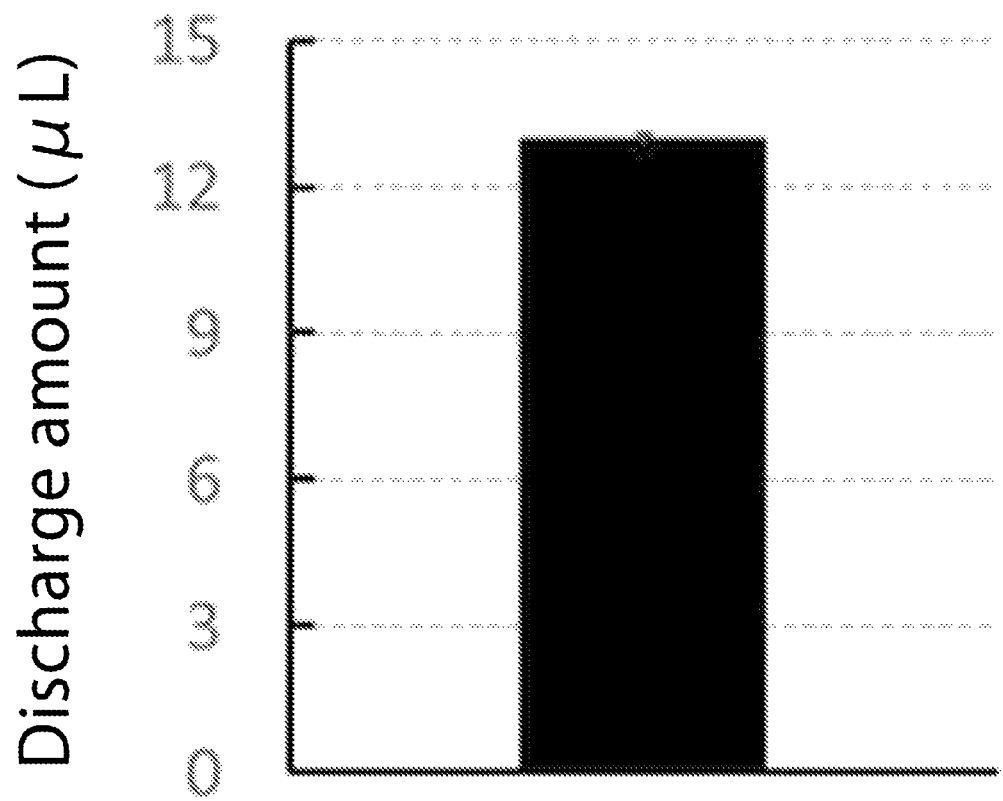

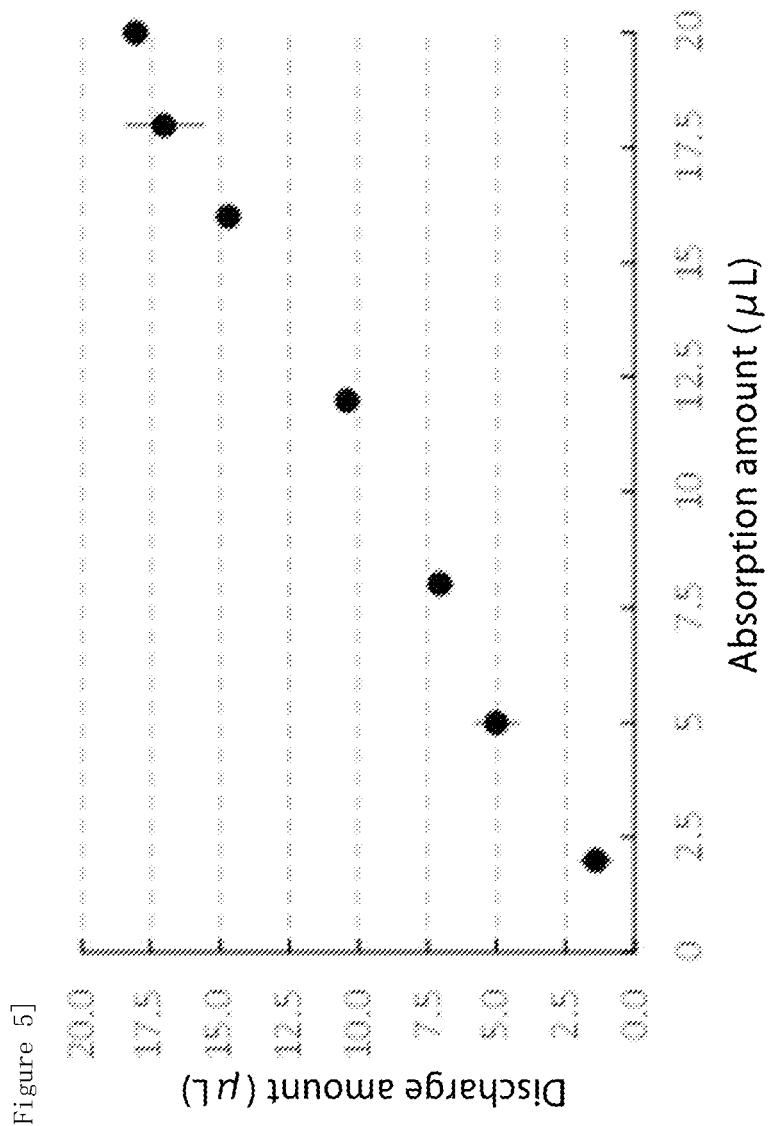
[Figure 5]

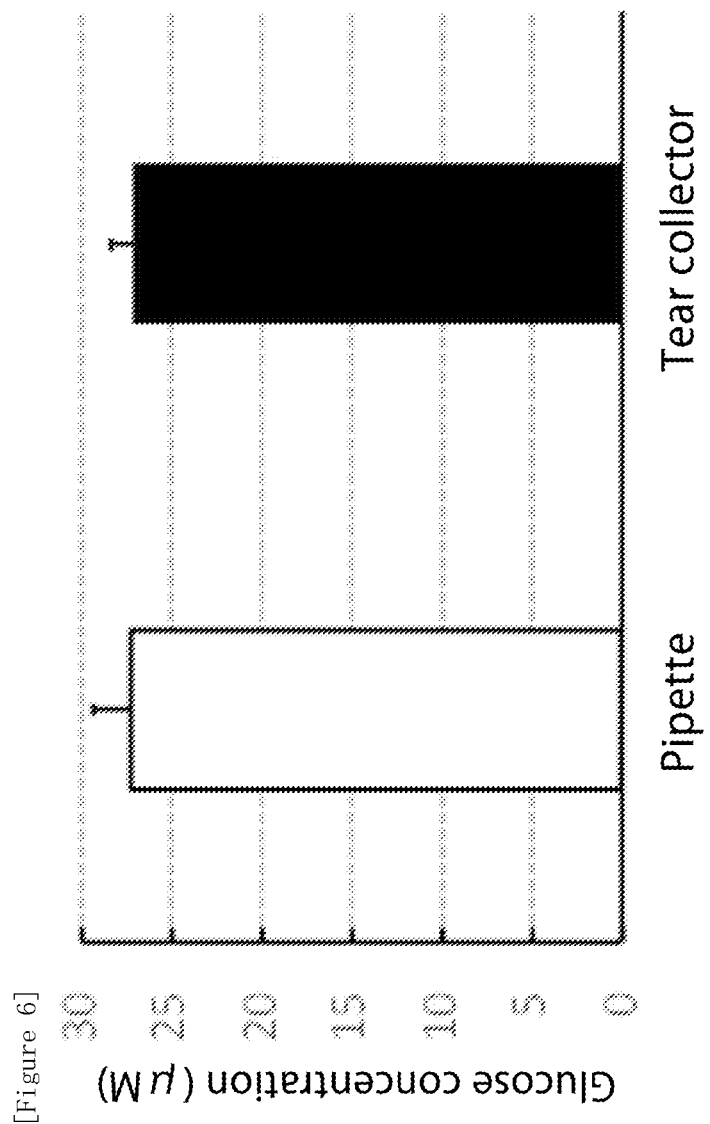
[Figure 6]

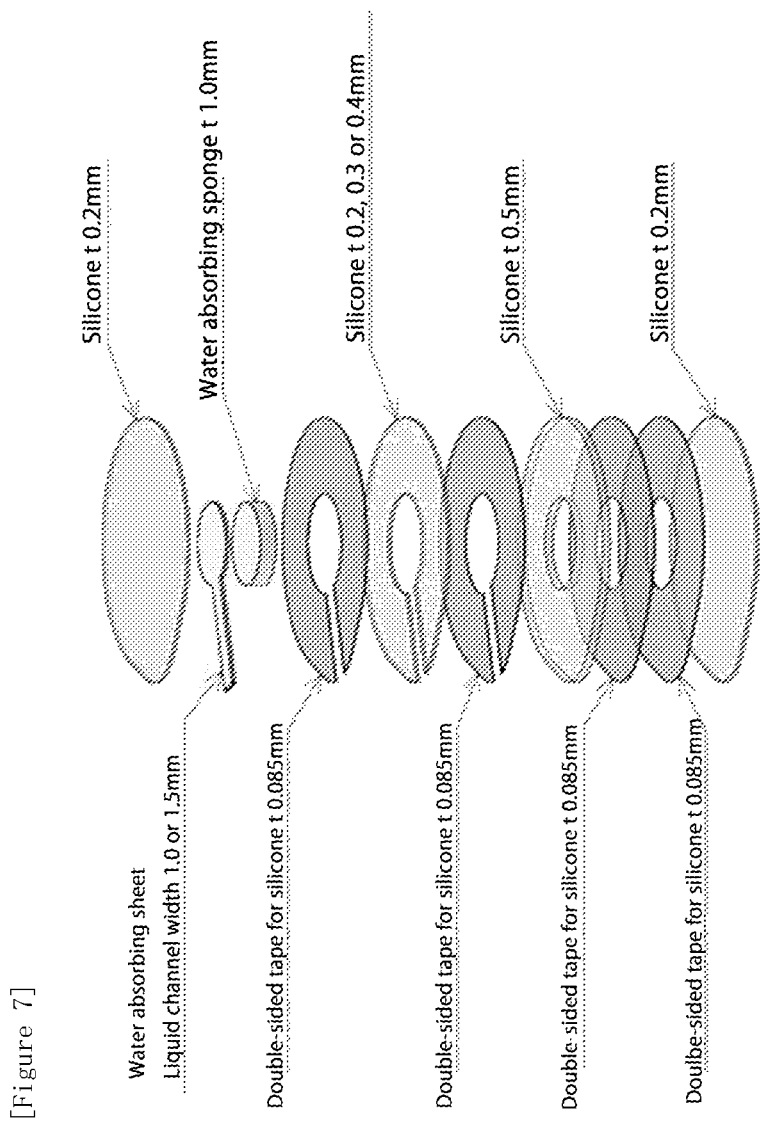

[Figure 8]
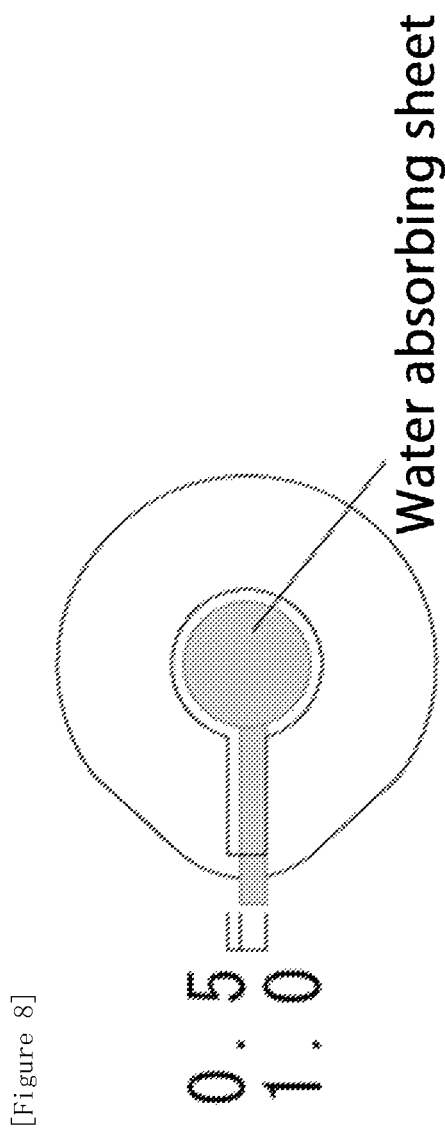

TRACE AMOUNT LIQUID SAMPLE COLLECTOR

TECHNICAL FIELD

The present invention relates to a device for collecting a trace amount of liquid sample.

BACKGROUND ART

As a method of collecting a trace amount of liquid sample such as tear or saliva, a capillary phenomenon of glass or resin is generally utilized, and for example, a sample liquid collection instrument having a capillary tube for taking in a sample and an air hole capable of being blocked at the other end (Patent Document 1) is disclosed. Further, there are disclosed a sampling device in which a sample is collected by a capillary tube in a capillary shape, and only a capillary portion is separated and inserted into a separately prepared container containing a predetermined amount of diluent (Patent Document 2), and a strip-shaped sampling and detection device in which IgE is detected by moving together the sample in contact with a labeling reagent which specifically binds to a substance to be detected by a capillary phenomenon (Patent Documents 3 and 4).

However, when a trace amount of body fluid or the like is collected using a liquid collection instrument known so far, there has been a risk of damaging the mucous membrane and the like of the living body. In addition, conventional liquid collection instruments are not specialized for collecting a trace sample, and it has been difficult to collect a sufficient amount of a trace sample. For example, in order to collect tears by a conventional method, a glass tube or a capillary tube made of plastic must be brought into contact with the eyeball, and there has been a risk of damaging some tissues of the eyeball in use, and a problem of feeling pain in contact with the eyeball. In addition, there has been a problem that a trace amount of tear was damaged by fear of contact with the eyeball.

PRIOR ART DOCUMENTS

Patent Documents

JP-A-2006-234446
JP-A-2012-26997
JP-A-2009-85839
JP-A-2010-243435

SUMMARY OF INVENTION

Technical Problem

As described above, it has been difficult to safely and sufficiently collect a trace sample such as tear fluid with the liquid collection instruments known so far.

Solving to Problem

As a result of extensive studies to solve the above problems, the present inventors have succeeded in developing a novel liquid sample collector capable of safely and sufficiently collecting a trace sample such as tear fluid (tear fluid, tears) in a sufficient amount.

The present invention relates to a trace-amount liquid sample collector, which is characterized in that the liquid sample collector comprises a main body and a first absorbent body, wherein the main body has at least one open end, wherein the main body includes an elastic hydrophobic material, wherein the first absorbent body is at least partially disposed in the main body, wherein the first absorbent body includes a water-absorbing material, and wherein the first absorbent body is disposed so as to contact the outside via the at least one open end of the main body.

In an embodiment of the present invention, it is characterized in that by bringing the absorbent body into contact with the trace sample, the trace sample is absorbed and retained by the absorbent body.

In an embodiment of the present invention, it is characterized in that by applying a pressure to the main body, then bringing the absorbent body into contact with the trace sample, and furthermore releasing the pressure applied to the main body, the trance sample is absorbed and retained in the absorbent body.

In an embodiment of the invention, it is characterized in that the liquid sample collector further comprises a second absorbent body, wherein the second absorbent body is at least partially disposed in the main body, wherein the second absorbent body includes a water-absorbing material, and wherein the second absorbent body is arranged at least partially in contact with the first absorbent body.

In an embodiment of the present invention, it is characterized in that the second absorbent body is configured to absorb a trace-amount liquid sample absorbed by the first absorbent body.

In an embodiment of the present invention, it is characterized in that, by applying a pressing force to the main body after collection of the trace liquid sample, the collected trace-amount liquid sample is discharged.

In an embodiment of the present invention, it is characterized in that the entire first absorbent body is disposed inside the main body.

In an embodiment of the present invention, it is characterized in that the entire second absorbent body is disposed inside the main body.

In an embodiment of the present invention, it is characterized in that the main body comprises a plurality of sheets, wherein at least one of the plurality of sheets includes an elastic hydrophobic material, and wherein the first absorbent body is disposed between the plurality of sheets.

In an embodiment of the present invention, it is characterized in that the main body further comprises a double-sided adhesive sheet, and the plurality of sheets are laminated via the double-sided adhesive sheet interposed therebetween.

In an embodiment of the present invention, it is characterized in that the inner surface of the main body in contact with the first absorbent body is formed of a hydrophobic material.

In an embodiment of the present invention, it is characterized in that the hydrophobic material is a material selected from the group consisting of natural rubber, synthetic rubber, and polysiloxane compounds.

In an embodiment of the invention, it is characterized in that the polysiloxane compound is silicone.

In an embodiment of the present invention, it is characterized in that the first absorbent body includes a water-absorbing material having a small volume expansion accompanied by absorption of a liquid.

In an embodiment of the present invention, it is characterized in that the first absorbent body includes a water-absorbing material having a small volume expansion accompanied by absorption of liquid, here the water-absorbing material having a small volume expansion accompanied by absorption of the liquid is fibrous, and is a material derived from a raw material selected from the group consisting of cellulose, polyurethane, polyvinyl alcohol, polyethylene, and polyolefin.

In an embodiment of the present invention, it is characterized in that the second absorbent body includes a water absorbing material having a large volume expansion accompanied by absorption of a liquid.

In an embodiment of the present invention, the second absorbent body includes a water absorbing material having a large volume expansion accompanied by absorption of a liquid, the water absorbing material having a large volume expansion accompanied by absorption of the liquid is porous, and is a material derived from a raw material selected from the group consisting of cellulose, polyurethane, polyvinyl alcohol, polyethylene, and polyolefin.

In an embodiment of the present invention, it is characterized in that the trace liquid sample is a tear fluid.

In an embodiment of the present invention, it is characterized in that the collector has a flow path leading from the open end to the inside of the main body, and the first absorbent body is disposed in the flow path, and the width of the first absorbent body is designed to be smaller than the width of the flow path.

An embodiment of the present invention is characterized in that it is designed to allow air to pass between the open end and the inside of the main body through a gap between the flow path and the first absorbent body.

The inventions optionally combining one or more features of the inventions described above are also included in the scope of the present invention.

Advantageous Effects of Invention

By having the above configurations, the liquid sample collector of the present invention can safely and quickly collect a sufficient amount of a trace sample such as tear fluid. In addition, unlike conventional liquid sample collection methods (e.g., the methods using a glass tube or a capillary), the liquid sample collector of the present invention can be sampled multiple times in one collector.

BRIEF DESCRIPTION OF DRAWINGS

FIG. 1 shows one embodiment of a liquid sample collector of the present invention.

FIG. 2 shows a design of an embodiment of a liquid sample collector of the present invention made in Example 2.

FIG. 3 shows a design of an embodiment of a liquid sample collector of the present invention made in Example 2.

FIG. 4 shows a graph showing the discharge of tear fluid when 20 μL of tear fluid was collected using the liquid sample collector of the present invention (mean discharge±standard error (μL)).

FIG. 5 shows a diagram plotting the relationship between the amount of water absorbed and the amount of discharge of the liquid sample collector of the present invention.

FIG. 6 shows a comparison of the glucose concentration in the tear fluid collected only with a pipette and in the tear fluid collected using a liquid sample collector of the present invention (white bar: using a pipette, black bar: using the collector of the present invention).

FIG. 7 shows a design of an embodiment of the liquid sample collector of the present invention made in Example 3.

FIG. 8 shows a design of an embodiment of the liquid sample collector of the present invention made in Example 3.

DESCRIPTION OF EMBODIMENTS

With reference to FIG. 1 which shows one embodiment of the present invention, the present invention will be explained below. The liquid sample collector of the present invention comprises a main body (a silicone sheet and an adhesive sheet of FIG. 1) and a first absorbent body (a water absorbing sponge or a water absorbing sheet of FIG. 1), the main body having at least one open end (a notch in the adhesive sheet of FIG. 1), the main body comprising a hydrophobic material having elasticity, the first absorbent body being disposed at least partially inside the main body, the first absorbent body comprising a water absorbing material, the first absorbent body being arranged so as to contact the outside via the at least one open end of said main body.

Although the size of the liquid sample collector of the present invention may be appropriately changed depending on the sample to be collected, for example, the maximum diameter of the sample collector may be designed to be, for example, 5 mm to 70 mm, preferably 8 mm to 50 mm, more preferably 10 mm to 30 mm, and most preferably 12 mm to 20 mm, as a main purpose is to collect trace liquid sample. If the maximum diameter of the collector falls below the lower limit of the above range, the amount of liquid that can be collected may be too small and possibly making it difficult to handle as a collector. If the maximum diameter of the collector exceeds the upper limit of the above range, the dead volume inside the collector may become large, possibly making it difficult to sufficiently collect trace sample.

The size of the open end and the flow path of the liquid sample collector of the present invention may be appropriately changed depending on the sample to be collected. But, for example, the width of the open end and the flow path may be designed to be 0.5 mm to 5 mm, preferably 0.75 mm to 4 mm, more preferably 1 mm to 3 mm, as a main purpose is to collect trace liquid sample. If the width of the open end and the flow path falls below the lower limit of the above range, the liquid absorbency of the collector of the present invention may be reduced. If the width of the open end and the flow path exceeds the upper limit of the above range, the dead volume in the flow path of the collector becomes large, possibly making it difficult to sufficiently collect trace sample.

It is preferable that the width of the absorbent body installed in the opening end portion and the flow path of the liquid sample collection device of the present invention is designed to be slightly smaller than the width of the opening end portion and the flow path. Designed in this way, there can be a gap between the open end and the flow path and the absorbent body through which air can pass, which improves the liquid absorption efficiency by the absorbent body. In addition, the liquid absorption efficiency can be maximized by designing an absorber slightly smaller than the width of the flow path to one side of the flow path and allowing air to pass between the open end of the collector and the inside of the main body through a gap between the flow path and the absorber. Further, the variation in absorption efficiency in the case of mass production can be reduced. Specifically, for example, the width of the absorbent body installed in the open end and the flow path of the collector can be designed to be 0.05 mm to 2 mm, preferably 0.1 mm to 1.5 mm, more preferably 0.3 mm to 1.0 mm, smaller than the width of the open end and the flow path.

As the material constituting the main body of the liquid sample collector of the present invention is not limited as long as it is a material having elasticity and having a property of hydrophobicity. But for example, a natural rubber, a synthetic rubber, or a polysiloxane compound (particularly, a silicone) can be used. By using a hydrophobic material as the main body of the collector, the loss (dead volume) of the sample when the liquid sample collected by the collector is discharged, can be reduced, thereby maximizing the collection amount of the trace sample. Further, by using a material having elasticity as a main body of the collector, a safe sample collection can be realized without damaging a mucosa or the like at the time of collecting a sample such as a body fluid.

In the example shown in FIG. 1, by adhering a plurality of silicone sheets by an adhesive sheet, a bag-shaped main body structure having elasticity and hydrophobicity is realized, but as long as the similar property and structure (a bag-shaped structure having elasticity and hydrophobicity) can be realized, the main body of the liquid sample collector of the present invention can be manufactured in various ways. For example, when a material such as a silicone sheet is subjected to surface treatment to directly bond a plurality of materials, an adhesive sheet in FIG. 1 becomes unnecessary. Also, for example, a mold or the like can be used by those skilled in the art to realize a seamless main body structure.

In the liquid sample collector of the present invention, a water absorbing body containing a water absorbing material is disposed inside the main body thereof, and the absorbent body is disposed so as to contact the outside via an open end portion of the collector main body.

Thus, when the liquid sample comes into contact with the open end portion of the liquid sample collector of the present invention, the liquid sample is absorbed by the water absorbing body containing the water absorbing material and is held inside the collector main body. The water absorbing body containing the water absorbing material in the collector of the present invention may be made of 1 kind of material, and may be manufactured using 2 or more kinds of materials. For example, as in the example shown in FIG. 1, a sheet-like first water absorbing body may be installed in the open end portion and the flow path of the collector main body, and a sponge-like second water absorbing body may be installed inside the collector main body, and the liquid absorbed from the outside by the first water absorbing body may be designed to be further absorbed by the second water absorbing body. In this manner, in the design of the liquid sample collector of the present invention, by using a combination of two or more types of water absorbing bodies having different properties, the absorption and retention of the liquid can be optimized, and the loss of the sample (dead volume) when the collected liquid is discharged can be reduced.

In the design of the liquid sample collector of the present invention, it is preferable that the water absorbing body installed in the open end and the flow path of the collector main body is a water absorbing material having a small volume expansion accompanied by absorption of the liquid. By using a water-absorbing material having a small volume expansion accompanied by the absorption of liquid as a water-absorbing member installed in the open end portion and the flow path of the collector main body, the liquid sample in the flow path or the like that remains when the liquid sample held inside the collector main body is discharged can be reduced, and the amount of the liquid sample to be collected can be maximized. Examples of a water-absorbing material having a small volume expansion accompanied by absorption of a liquid include a fibrous material. Although there is no limitation on the raw material of the fibrous material used as the water absorbing body in the present invention, for example, a raw material using cellulose, polyurethane, polyvinyl alcohol, polyethylene, or polyolefin as a raw material may be used. As long as such an absorbent body has a desired property, a commercially available material may be used.

In the design of the liquid sample collector of the present invention, it is preferable that the water absorbing body installed inside the collector main body is a water absorbing material having a large volume expansion accompanied by absorption of the liquid. By using a water absorbing material having a large volume expansion accompanied by absorption of liquid as a water absorbing body installed inside the collector main body, the liquid absorbency and retention of the collector of the present invention can be improved. Examples of the water-absorbing material having a large volume expansion accompanied by absorption of liquid include a material having a porous property. Although there is no limitation on the raw material of the porous material used as the water absorbing body in the present invention, for example, a raw material using cellulose, polyurethane, polyvinyl alcohol, polyethylene, or polyolefin as a raw material may be used. As long as such an absorbent body has a desired property, a commercially available material may be used.

Although the collector of the present invention is suitable for collection of various trace liquid samples, as described above, the collector of the present invention is particularly suitable for collection of body fluids because of its reduced invasiveness to the living body. The living body may be an outer skin, may be an epidermis, and may be an epithelium. The outer skin or the like of the living body may be the skin, epidermis or mucous membrane of an animal. The animal may be a human. The body fluid may be lymph fluid, tissue fluid such as interstitial fluid, intercellular fluid, interstitial fluid, and the like, and may be body cavity fluid, serosal fluid, pleural fluid, ascites fluid, capsular fluid, cerebrospinal fluid, joint fluid (synovial fluid), and aqueous humor of the eye (aqueous humor). The body fluid may be digestive fluid such as saliva, gastric juice, bile, pancreatic juice, intestinal fluid, etc., and may be sweat, tears, nasal mucus, urine, semen, vaginal fluid, amniotic fluid, milk, etc. In some embodiments, bodily fluids may be collected from organs in the body. The surface of the living body to be approached may be a surface of an internal organ or an organ that has appeared by incision or the like, and may be a tissue surface inside the same. In another embodiment, a medical device or a device or the like which is inserted into a living body may be used without incision to reach a predetermined portion in the body to collect body fluid. Further, as described above, since the collector of the present invention can collect trace sample without loss, it is more suitable for collecting body fluid (e.g., tear fluid) having a small amount of secretion.

The terms used herein are used to describe specific embodiments, except as specifically defined, and are not intended to limit the invention.

Also, the term "comprising" as used herein is intended to include the recited material (e.g., elements, steps, elements, numbers), and the like, unless the context clearly dictates otherwise, and does not exclude the presence of other material (e.g., elements, steps, elements, numbers), and the like.

Unless defined otherwise, all terms (including technical and scientific terms) used herein have the same meaning as commonly understood by a person having ordinary skill in the art to which this invention belongs. The terms used herein should be construed as having a meaning consistent with their meaning in this specification and the related art, and should not be construed in an idealized or overly formal sense, unless a different definition clearly dictates otherwise.

In the following, the invention will be explained in more detail with reference to examples. However, the present invention may be embodied in various embodiments and should not be construed as limited to the examples set forth herein.

EXAMPLES

Example 1: Liquid Sample Collector of the Present Invention

The structure of a liquid sample collector according to an embodiment of the present invention, is shown in FIG. 1. This embodiment is an example in which the dead volume is reduced by using two types of water absorbing materials inside the collector.

The main body of the collector has a bag-like structure in which the peripheral edge portions of two silicone sheets cut in a droplet shape that easily comes into contact with a portion such as the eyebrows and the eyebrows are bonded together by an adhesive sheet, and a part of the peripheral edge portions of the silicone sheets is not bonded, forming an open end portion (the adhesive sheet can be omitted when the silicone sheets are directly bonded by surface treatment). A fibrous absorbent sheet having a small volume expansion is disposed inside the main body, and the absorbent sheet communicates with the inside of the main body while a part of the absorbent sheet is exposed to the outside from the open end. A foam water absorbing sponge is disposed inside the bag-shaped main body, and the water absorbing sponge increases in volume with absorption of liquid. The absorbent sheet and the absorbent sponge are in direct contact with each other in the interior of the main body. With such a structure, the water-absorbing sponge can collect liquid a plurality of times until its volume increases and reaches the maximum value, and when the bag-shaped collector inflated by the volume expansion is pressed, the liquid is discharged from the open end.

Note that, in this embodiment, a water absorbing sheet was made of Kimwipe™ (S-200, Nippon Paper Crecia Co., Ltd.), which is a thin paper of a pulp material, and a water absorbing sponge was made of a sheet having a thickness of 1 mm of Sofras™ (manufactured by AION Co., Ltd.), which is a polyurethane sponge, processed into a diameter of 5 mm.

The collector in this example could easily collect human tears. In other words, when the tear fluid was brought into contact with the water absorbing sheet exposed from the open end portion, the tear fluid was absorbed into the inside of the collector main body via the water absorbing sheet and further absorbed into the water absorbing sponge in direct contact with the water absorbing sheet. Then, after collecting the tear fluid, the collector main body was pressed, and when the water absorbing sponge was squeezed, the tear fluid was discharged from the open end portion. By using a soft thin paper of pulp material as a water absorbing sheet, the dead volume inside the collector was reduced, and there was no feeling of pain when the collector came into contact with the eye when the tear fluid was collected. Further, by using a polyurethane sponge as a water absorbing sponge, which has a volume expansion rate which is large to some extent at the time of water absorption and has a restoring force after discharge, a necessary and sufficient amount of tear fluid could be collected.

Tear fluid was collected in this example, but also the collector of the present invention can be used for collecting body fluids such as sweat, saliva, nasal mucus and the like.

Example 2: Performance Evaluation of a Liquid Collector of the Present Invention To evaluate the performance of the liquid collector of the present invention, a collector based on the design shown in FIGS. 2 and 3 was fabricated. The collector was made by sandwiching a 0.5 mm silicone rubber sheet for forming a space for absorbing sponge and water-absorbing sheet and a 0.2 mm thick silicone rubber sheet for forming a flow path, with a 0.2 mm thick silicone rubber sheets from both sides and gluing each with a 0.085 mm thick film double-sided tape (#7082, Teraoka Works, Ltd.) suited for adhesion of silicone rubber. In addition, for the water absorbing sponge, a Sofras sheet (thickness: 1 mm, AION Co., Ltd.) which is a polyurethane sponge was cut out into a circle having a diameter of 5 mm, and for the water absorbing sheet, a Kimwipe (S-200, Nippon Paper Crecia Co., Ltd.) which is a thin paper of a pulp material was cut out into a keyhole shape (circle: diameter 5 mm, bar portion: 1.5×8.5 mm) was used.

Tear fluid was collected by touching 20 µL of tear previously dropped on a Petri dish (previously collected and stored at 4° C.) with a slightly exposed water absorbing sheet from the open end of the collector (unused) made by the above method. The tear was all absorbed into the water-absorbing sponge inside the main body via the water-absorbing sheet. Next, the tear fluid was discharged by pressing the finger on the central portion of the main body of the collector in which the tear fluid was absorbed (near the top of the water-absorbing sponge) was pressed by fingers to discharge the tear fluid into a petri dish set on an electronic balance, and the mass of the discharged tear fluid was measured, whereby the actual discharge amount was estimated from the specific gravity of the tear fluid.

FIG. 4 is a graph showing the discharged amount of tear fluid using the collector based on the above design (mean discharge amount±standard error (µL)). When 20 µL of tear fluid was sucked into the collector, the mean discharge amount was 12.9±0.15 µL (N=4). This means that the amount of liquid that could not be discharged was 35.5%, but the coefficient of variation representing the variation of each discharged amount was 2.3%, which was very good.

Next, after the tear fluid was once absorbed and discharged, the collector was subsequently used repeatedly, and the amount of absorbed water and the average amount of discharged water were examined. After 20 µL of tear fluid was sucked into and discharged from the unused collector device, the same collector device was used to repeatedly absorb and discharge tear fluid in the range of 2-20 µL, and the mass at that time was measured, thereby estimating the amount of tear fluid actually discharged from the specific gravity of the tear fluid.

FIG. 5 shows a plot of the relationship between water intake and discharge amounts of the collector of the present invention (discharge±standard error (µL)). When the collector did once intake and discharge and then was repeatedly used, it was confirmed that the mean discharge amount increased in a manner dependent on the amount of water absorbed (20 µL; 18.1±0.4 µL, 18 µL; 17.0±1.4 µL, 16 µL; 14.7±0.3 µL, 12 µL; 10.4±0.4 µL, 8 µL; 7.1±0.2 µL, 5 µL; 5.0±0.8 µL, 2 µL; 1.4±0.6 µL), and the mean discharge rate was as high as 88.9% (N=4). From the above results, it has been shown that the liquid sample collector of the present invention is extremely suitable for collecting trace liquid sample.

Next, it was examined by measuring glucose in tear fluid whether the concentration of the substance in the body fluid does not change before and after performing the collection using the collector of the present invention. Tear fluid previously dropped on a petri dish (tear fluid previously collected and pooled) were collected using the collector of the present invention and discharged into a tube. In addition, the tear fluid serving as a control was previously dropped on a petri dish in the same manner, and was collected using a pipette. Then, the collected tear samples were analyzed using high-performance liquid chromatography (Alliance e2695, Waters2465, Nippon Waters Co., Ltd.) to estimate the glucose levels in each tear sample.

FIG. 6 shows a comparison of the glucose concentration of tear fluid collected using a pipette only and tear fluid collected using the collector of the present invention (white bar: using a pipette, black bar: using the collector of the present invention). The glucose concentration in the tear fluid collected using the collector of the present invention was $27.1 \pm 1.3$ µM (N=4) On the other hand, the concentration of glucose in the tear fluid collected using pipettes was $27.3 \pm 2.1$ µM (N=3), and there were no significant differences between the two (Student's t-test; p=0.94). The above results suggest that the use of the collector of the present invention does not affect the component concentration of the collected body fluid.

Example 3: Study of the Flow Path Width and Performance of a Liquid Sample Collector In order to evaluate the relationship between the flow width and the performance of the collector of the present invention, the water absorption rate of tear fluid when the size of the flow path and the water absorbing sheet was changed was studied. The water absorption rate was evaluated by comparing the time taken for absorbing 20 µL of tear fluid dropped on a petri dish beforehand in the same manner as in Example 2, from the design of the collector shown in FIG. 3, (i) when a 0.2 mm thick silicone rubber sheet for forming the flow path was changed to 0.3, 0.4, or 1.0 mm (FIG. 7), (ii) when the width of the water absorption sheet was changed from 1.0 mm to 1.5 mm (FIG. 7), and (iii) when the shape of the water absorption sheet was changed to a shape that sufficiently opens the flow path on one side (FIG. 8).

First, when the silicone sheet thickness for forming the flow path was increased from 0.2 mm to 0.4 mm (above (i)), the absorption speed became slightly faster. However, when the silicone thickness was extremely increased, such as 1.0 mm, the water absorption speed did not become faster, indicating a decrease in discharge (with 20 µL of water absorption, 9.4 µL of discharge). On the other hand, when the width of the water-absorbing sheet was widened to the full flow path (from 1.0 to 1.5 mm) (above (ii)), water could not be absorbed as quickly as the speed of the water-absorbing sheet having the width of 1.0 mm. From the above results, it was suggested that a certain gap is necessary for the flow path, but even if the flow path is excessively widened, it may not be effective. Therefore, in order to maximize the space of the flow path portion in a state in which the water absorbing sheet is placed, the water absorbing sheet was designed so as to be arranged so that the water absorbing sheet is brought closer to one side of the flow path (above (iii), FIG. 8).

Compared with the arrangement of a water absorbing sheet of 1.0 mm width was placed in the center of the flow path, a further improvement in the water absorbing rate was confirmed in the collector designed to dispose the water absorbing sheet on one side of the flow path. From the above results, it is suggested that in the case of designing the liquid sample collector of the present invention as shown in FIG. 2, it is preferable to design the silicone sheet in the flow path portion to have an arrangement in which the silicone sheet is 0.5 mm and the width of the water absorbing sheet is 1.0 mm and the silicone sheet is shifted to one side of the flow path (i.e., an arrangement in which an appropriate gap exists between the open end of the collector and the water absorbing sheet).

Example 4: About the Water-Absorbing Sponge and the Water-Absorbing Sheet Inside the Sample Collector The performance of the liquid sample collector of the present invention and the relationship between the water absorbing sponge and the water absorbing sheet were studied. The collector was designed based on Examples 1 and 2. As a basic design, Sofras (1 mm thick, AION Co., Ltd.), a polyurethane sponge, and fibrous filter paper (Whatman #41, GE healthcare) were used as water absorption sponges, and the performance of the basic design was compared and examined by changing the respective members. The performance evaluation of the body fluid collector was confirmed by measuring the water absorption rate when 20 µL of tear fluid previously added to the petri dish was collected by the body fluid collector in the same manner as in Example 1, and the discharge amount when the central portion was pressed thereafter.

First, a case in which only the water absorbing sheet was used without a water absorbing sponge was examined. When 20 µL of tear fluid was collected using a collector in which only one sheet of filter paper as a water absorbing sheet was inserted, the water absorption rate was considerably slower than when a water absorbing sponge was put in, and also flowed out from the tip by a small pressing, and thus tear fluid of 20 µL min could not be appropriately retained. On the other hand, the discharge amount was 12 µL, which was not significantly different from the usual sampling device.

As described above, it has been shown that the use of a porous water-absorbing material with a large volume expansion accompanied by the absorption of liquid as a water-absorptive sponge can improve the function of the collector of the present invention.

Next, the case in which the water absorption sponge was changed to filter paper was examined. When tear fluid was collected in a body fluid collector containing 1 sheet of filter paper processed into a keyhole shape as a water absorbing sheet and 5 sheets of filter paper cut into a circle having a diameter of 5 mm so as to have a total thickness of about 1 mm as a water absorbing sponge, the water absorbing rate was not very different from that in the case where Sofras was put in as a water absorbing sponge, but it became clear that there was a considerable dead volume of 6.4 µL when the filter paper was discharged by pressing. In addition, when 20 µL was sucked again, the discharge amount was 13.7 µL, which was much smaller than that of a normal body fluid collector. As described above, it has also been shown that, by using a porous water absorbing material having a large volume expansion accompanied by absorption of liquid as a water absorbing sponge, a dead volume at the time of liquid discharge decreases in the collector of the present invention.

Finally, a case was examined in which Sofras, a polyurethane sponge, was cut into a keyhole shape and inserted as a water absorbing sheet was examined. When the tear fluid was collected by a collector in which Sofras was cut in a key form and inserted, the water absorption speed was somewhat slower than that of a collector in which a normal water absorbing sheet (filter paper or the like) and a water absorbing sponge (polyurethane sponge or the like) were used in combination. On the other hand, the discharge amount was 5.4 µL, which was quite poor. In addition, when a sufficient amount of tear fluid was absorbed into an unused body fluid collector, the discharge amount when pressed in a normal tear collector was about 24 µL, but the discharge amount was slightly smaller in a collector made using Sofras as a water absorbing sheet, and was about 21 µL. These results showed that the dead volume that appeared in the flow path during the discharge of the liquid can be reduced by using a fibrous water-absorbing material having a small volume expansion accompanied by the absorption of the liquid as the water-absorbing sheet.

From the above results, it has been shown that it is preferable to use a porous water-absorbing material having a large volume expansion accompanied by absorption of liquid as a water-absorbing sponge, and to use a fibrous water-absorbing material having a small volume expansion accompanied by absorption of a liquid as a water-absorbing sheet, from the viewpoint of absorbency and retention of liquid and reduction of a dead volume during the discharge of the liquid.

The invention claimed is:

1. A trace-amount liquid sample collector, comprising:
   a main body, a first absorbent body, and a second absorbent body,
   wherein the main body has at least one open end,
   wherein the main body includes an elastic hydrophobic material,
   wherein the first absorbent body is at least partially disposed inside the main body,
   wherein the first absorbent body includes a first water-absorbing material, and
   wherein the first absorbent body is disposed so as to contact the outside via the at least one open end of the main body,
   wherein the trace-amount liquid sample collector has a flow path leading from the open end to the inside of the main body,
   wherein the first absorbent body is disposed in the flow path,
   wherein a width of the first absorbent body is designed to be smaller than a width of the flow path,
   wherein the first absorbent body is designed to allow air to pass between the open end and the inside of the main body through a gap between the flow path and the first absorbent body,
   wherein the second absorbent body is at least partially disposed in the main body,
   wherein the second absorbent body includes a second water-absorbing material, and
   wherein the second absorbent body is disposed at least partially in contact with the first absorbent body.

2. The trace-amount liquid sample collector of claim 1, wherein upon contacting the first absorbent body with a trace sample, the first absorbent body is configured to absorb and retain the trace sample in the first absorbent body.

3. The trace-amount liquid sample collector of claim 2, wherein upon applying a pressure to the main body, then bringing the first absorbent body into contact with the trace sample, and releasing the pressure applied to the main body, the first absorbent body is configured to absorb and retain the trace sample in the first absorbent body.

4. The trace-amount liquid sample collector of claim 1, wherein the second absorbent body is configured to absorb a trace-amount liquid sample absorbed by the first absorbent body.

5. The trace-amount liquid sample collector of claim 1, wherein the trace-amount liquid sample collector is configured such that by applying a pressing force to the main body after collection of a trace-amount liquid sample, the collected trace-amount liquid sample is discharged.

6. The trace-amount liquid sample collector of claim 1, wherein the entire first absorbent body is disposed inside the main body.

7. The trace-amount liquid sample collector of claim 1, wherein the entire second absorbent body is disposed inside the main body.

8. The trace-amount liquid sample collector of claim 1, wherein the main body comprises a plurality of sheets, wherein at least one of the plurality of sheets comprises the elastic hydrophobic material, and wherein the first absorbent body is disposed between the plurality of sheets.

9. The trace-amount liquid sample collector of claim 8, wherein the main body further comprises a double-sided adhesive sheet, and wherein the plurality of sheets are laminated via the double-sided adhesive sheet interposed therebetween.

10. The trace-amount liquid sample collector of claim 1, wherein an inner surface of the main body in contact with the first absorbent body is formed of the elastic hydrophobic material.

11. The trace-amount liquid sample collector of claim 1, wherein the elastic hydrophobic material is a material selected from the group consisting of a natural rubber, a synthetic rubber, and a polysiloxane compound.

12. The trace-amount liquid sample collector of claim 11, wherein the polysiloxane compound is silicone.

13. The trace-amount liquid sample collector of claim 1, wherein the first water-absorbing material has a small volume expansion accompanied by absorption of a liquid.

14. The trace-amount liquid sample collector of claim 1, wherein the first water-absorbing material has a small volume expansion accompanied by absorption of a liquid, and wherein the first water-absorbing material is fibrous, and is a material derived from a raw material selected from the group consisting of cellulose, polyurethane, polyvinyl alcohol, polyethylene, and polyolefin.

15. The trace-amount liquid sample collector of claim 1, wherein the trace-amount liquid sample collector is configured to collect a tear fluid.

* * * * *